US011161896B2

(12) United States Patent
He et al.

(10) Patent No.: US 11,161,896 B2
(45) Date of Patent: Nov. 2, 2021

(54) ANTIBODIES FOR DETECTION OF COLISTIN-RESISTANCE

(71) Applicant: The United States of America, as represented by the Secretary of Agriculture, Washington, DC (US)

(72) Inventors: Xiaohua He, Richmond, CA (US); Daniela Mavrici, Oakland, CA (US)

(73) Assignee: The United States of America, as represented by the Secretary of Agriculture, Washington, DC (US)

(*) Notice: Subject to any disclaimer, the term of this patent is extended or adjusted under 35 U.S.C. 154(b) by 84 days.

(21) Appl. No.: 16/353,467

(22) Filed: Mar. 14, 2019

(65) Prior Publication Data

US 2019/0322727 A1 Oct. 24, 2019

Related U.S. Application Data

(60) Provisional application No. 62/660,490, filed on Apr. 20, 2018.

(51) Int. Cl.
| | | |
|---|---|---|
| *G01N 33/569* | (2006.01) | |
| *C07K 16/12* | (2006.01) | |
| *G01N 33/68* | (2006.01) | |

(52) U.S. Cl.
CPC .... *C07K 16/1217* (2013.01); *G01N 33/56911* (2013.01); *G01N 33/6845* (2013.01); *C07K 2317/10* (2013.01); *C07K 2317/24* (2013.01)

(58) Field of Classification Search
None
See application file for complete search history.

(56) References Cited

PUBLICATIONS

Protein design vol. 22, pp. 159-168, 2009 (Year: 2009).*
Goel et al. J. Immunonlogy voi. 173, No. 12, pp. 7358-7367, 2004 (Year: 2004).*
Bettelheim, K. A. and Beutin L., 2003, "Rapid laboratory identification and characterization of verocytotoxigenic (Shiga toxin producing) *Escherichia coli* (VTEC/STEC)," J. Appl. Microbiol. 95(2): 205-217.
Castanheira, M., et al., 2016, "Effect of the µ-Lactamase Inhibitor Vaborbactam Combined with Meropenem against Serine Carbapenemase-Producing Enterobacteriaceae," Antimicrob. Agents Chemother. 60(9): 5623-5624.
Catry, B., et al., 2015, "Use of colistin-containing products within the European Union and European Economic Area (EU/EEA): development of resistance in animals and possible impact on human and animal health," Int. J. Antimicrob. Agents 46(3): 297-306.
Du, H., et al., 2016, "Emergence of the mcr-1 colistin resistance gene in carbapenem-resistant Enterobacteriaceae," Lancet Infect. Dis. 16(3): 287-288.
Fach, P., et al., 2003, "Comparison of different PCR tests for detecting Shiga toxin-producing *Escherichia coli* O157 and development of an ELISA-PCR assay for specific identification of the bacteria," J. Microbiol. Methods 55(2): 383-392.
Karch, H., et al., 1992, "Frequent loss of Shiga-like toxin genes in clinical isolates of *Escherichia coli* upon subcultivation," Infect. Immun 60(8): 3464-3467.
Kline, K. E., et al., 2016, "Investigation of First Identified mcr-1 Gene in an Isolate From a U.S. Patient—Pennsylvania, 2016," MMWR Morb. Mortal. Wkly. Rep. 65(36): 977-978.
Lee, H., et al., 2004, "The PmrA-Regulated pmrC Gene Mediates Phosphoethanolamine Modification of Lipid A and Polymyxin Resistance in *Salmonella enterica*," J. Bacteriol. 186(13): 4124-4133.
Liu, Y. Y., et al., 2016, "Emergence of plasmid-mediated colistin resistance mechanism MCR-1 in animals and human beings in China: a microbiological and molecular biological study," Lancet Infect. Dis. 16(2): 161-168.
McGann, P., et al., 2016, "*Escherichia coli* Harboring mcr-1 and blaCTX-M on a Novel IncF Plasmid: First Report of mcr-1 in the United States," Antimicrob. Agents Chemother. 60(7): 4420-4421.
Mediavilla, J. R., et al., 2016, "Colistin- and Carbapenem-Resistant *Escherichia coli* Harboring mcr-1 and blaNDM-5' Causing a Complicated Urinary Tract Infection in a Patient from the United States," mBio 7(4).
Meinersmann, R. J., et al., 2017, "Prevalence of mcr-1 in the Cecal Contents of Food Animals in the United States," Antimicrob. Agents Chemother. 61(2).
Stojanoski, V., et al., 2016, "Structure of the catalytic domain of the colistin resistance enzyme MCR-1," BMC Biol. 14(1): 81.
Trent, M. S., et al., 2001, "An Inner Membrane Enzyme in *Salmonella* and *Escherichia coli* That Transfers 4-Amino-4-deoxy-L-arabinose to Lipid A: Induction in Polymyxin-Resistant Mutants and Role of a Novel Lipid-Linked Donor," J. Biol. Chem. 276(46): 43122-43131.
Vasquez, A. M., et al., 2016, "Investigation of *Escherichia coli* Harboring the mcr-1 Resistance Gene—Connecticut, 2016," MMWR Morb. Mortal. Wkly. Rep 65(36): 979-980. Wertheim, H., et al., 2013, "Global survey of polymyxin use: A call for international guidelines," J. Glob. Antimicrob. Resist. 1(3): 131-134.
Xavier, B. B., et al., 2016, "Identification of a novel plasmid-mediated colistin-resistance gene, mcr-2, in *Escherichia coli*, Belgium, Jun. 2016," Euro Surveill. 21(27).

* cited by examiner

*Primary Examiner* — Jana A Hines
*Assistant Examiner* — Khatol S Shahnan Shah
(74) *Attorney, Agent, or Firm* — John Fado; Maria Restrepo-Hartwig

(57) ABSTRACT

Monoclonal antibodies against bacterial proteins that confer resistance to the antibiotic colistin and hybridomas that produce such monoclonal antibodies are described. The monoclonal antibodies have a strong affinity for MCR proteins and may be used in detection methods and kits to detect the presence of MCR proteins including variants thereof in a sample.

7 Claims, 8 Drawing Sheets
Specification includes a Sequence Listing.

SEQUENCE LISTING

<160> NUMBER OF SEQ ID NOS: 8

<210> SEQ ID NO 1
<211> LENGTH: 541
<212> TYPE: PRT
<213> ORGANISM: Escherichia coli

<400> SEQUENCE: 1

```
Met Met Gln His Thr Ser Val Trp Tyr Arg Arg Ser Val Ser Pro Phe
1               5                   10                  15

Val Leu Val Ala Ser Val Ala Val Phe Leu Thr Ala Thr Ala Asn Leu
            20                  25                  30

Thr Phe Phe Asp Lys Ile Ser Gln Thr Tyr Pro Ile Ala Asp Asn Leu
        35                  40                  45

Gly Phe Val Leu Thr Ile Ala Val Val Leu Phe Gly Ala Met Leu Leu
    50                  55                  60

Ile Thr Thr Leu Leu Ser Ser Tyr Arg Tyr Val Leu Lys Pro Val Leu
65                  70                  75                  80

Ile Leu Leu Leu Ile Met Gly Ala Val Thr Ser Tyr Phe Thr Asp Thr
                85                  90                  95

Tyr Gly Thr Val Tyr Asp Thr Thr Met Leu Gln Asn Ala Leu Gln Thr
            100                 105                 110

Asp Gln Ala Glu Thr Lys Asp Leu Leu Asn Ala Ala Phe Ile Met Arg
        115                 120                 125

Ile Ile Gly Leu Gly Val Leu Pro Ser Leu Leu Val Ala Phe Val Lys
    130                 135                 140

Val Asp Tyr Pro Thr Trp Gly Lys Gly Leu Met Arg Arg Leu Gly Leu
145                 150                 155                 160
```

```
Ile Val Ala Ser Leu Ala Leu Ile Leu Leu Pro Val Val Ala Phe Ser
                165                 170                 175

Ser His Tyr Ala Ser Phe Phe Arg Val His Lys Pro Leu Arg Ser Tyr
            180                 185                 190

Val Asn Pro Ile Met Pro Ile Tyr Ser Val Gly Lys Leu Ala Ser Ile
            195                 200                 205

Glu Tyr Lys Lys Ala Ser Ala Pro Lys Asp Thr Ile Tyr His Ala Lys
            210                 215                 220

Asp Ala Val Gln Ala Thr Lys Pro Asp Met Arg Lys Pro Arg Leu Val
225                 230                 235                 240

Val Phe Val Val Gly Glu Thr Ala Arg Ala Asp His Val Ser Phe Asn
                245                 250                 255

Gly Tyr Glu Arg Asp Thr Phe Pro Gln Leu Ala Lys Ile Asp Gly Val
            260                 265                 270

Thr Asn Phe Ser Asn Val Thr Ser Cys Gly Thr Ser Thr Ala Tyr Ser
        275                 280                 285

Val Pro Cys Met Phe Ser Tyr Leu Gly Ala Asp Glu Tyr Asp Val Asp
        290                 295                 300

Thr Ala Lys Tyr Gln Glu Asn Val Leu Asp Thr Leu Asp Arg Leu Gly
305                 310                 315                 320

Val Ser Ile Leu Trp Arg Asp Asn Asn Ser Asp Ser Lys Gly Val Met
                325                 330                 335

Asp Lys Leu Pro Lys Ala Gln Phe Ala Asp Tyr Lys Ser Ala Thr Asn
            340                 345                 350

Asn Ala Ile Cys Asn Thr Asn Pro Tyr Asn Glu Cys Arg Asp Val Gly
            355                 360                 365

Met Leu Val Gly Leu Asp Asp Phe Val Ala Ala Asn Asn Gly Lys Asp
    370                 375                 380

Met Leu Ile Met Leu His Gln Met Gly Asn His Gly Pro Ala Tyr Phe
385                 390                 395                 400

Lys Arg Tyr Asp Glu Lys Phe Ala Lys Phe Thr Pro Val Cys Glu Gly
            405                 410                 415

Asn Glu Leu Ala Lys Cys Glu His Gln Ser Leu Ile Asn Ala Tyr Asp
            420                 425                 430

Asn Ala Leu Leu Ala Thr Asp Asp Phe Ile Ala Gln Ser Ile Gln Trp
        435                 440                 445

Leu Gln Thr His Ser Asn Ala Tyr Asp Val Ser Met Leu Tyr Val Ser
        450                 455                 460

Asp His Gly Glu Ser Leu Gly Glu Asn Gly Val Tyr Leu His Gly Met
465                 470                 475                 480

Pro Asn Ala Phe Ala Pro Lys Glu Gln Arg Ser Val Pro Ala Phe Phe
                485                 490                 495

Trp Thr Asp Lys Gln Thr Gly Ile Thr Pro Met Ala Thr Asp Thr Val
            500                 505                 510

Leu Thr His Asp Ala Ile Thr Pro Thr Leu Leu Lys Leu Phe Asp Val
        515                 520                 525

Thr Ala Asp Lys Val Lys Asp Arg Thr Ala Phe Ile Arg
530                 535                 540
```

<210> SEQ ID NO 2
<211> LENGTH: 538
<212> TYPE: PRT
<213> ORGANISM: Escherichia coli

<400> SEQUENCE: 2

```
Met Thr Ser His His Ser Trp Tyr Arg Tyr Ser Ile Asn Pro Phe Val
1               5                   10                  15

Leu Met Gly Leu Val Ala Leu Phe Leu Ala Ala Thr Ala Asn Leu Thr
            20                  25                  30

Phe Phe Glu Lys Ala Met Ala Val Tyr Pro Val Ser Asp Asn Leu Gly
        35                  40                  45

Phe Ile Ile Ser Met Ala Val Ala Val Met Gly Ala Met Leu Leu Ile
        50                  55                  60

Val Val Leu Leu Ser Tyr Arg Tyr Val Leu Lys Pro Val Leu Ile Leu
65              70                  75                      80

Leu Leu Ile Met Gly Ala Val Thr Ser Tyr Phe Thr Asp Thr Tyr Gly
                85                  90                  95

Thr Val Tyr Asp Thr Thr Met Leu Gln Asn Ala Met Gln Thr Asp Gln
                100                 105                 110

Ala Glu Ser Lys Asp Leu Met Asn Leu Ala Phe Phe Val Arg Ile Ile
            115                 120                 125

Gly Leu Gly Val Leu Pro Ser Val Leu Val Ala Val Ala Lys Val Asn
        130                 135                 140

Tyr Pro Thr Trp Gly Lys Gly Leu Ile Gln Arg Ala Met Thr Trp Gly
145                 150                 155                 160

Val Ser Leu Val Leu Leu Leu Val Pro Ile Gly Leu Phe Ser Ser Gln
                165                 170                 175

Tyr Ala Ser Phe Phe Arg Val His Lys Pro Val Arg Phe Tyr Ile Asn
                180                 185                 190

Pro Ile Thr Pro Ile Tyr Ser Val Gly Lys Leu Ala Ser Ile Glu Tyr
            195                 200                 205

Lys Lys Ala Thr Ala Pro Thr Asp Thr Ile Tyr His Ala Lys Asp Ala
        210                 215                 220

Val Gln Thr Thr Lys Pro Ser Glu Arg Lys Pro Arg Leu Val Val Phe
225                 230                 235                 240

Val Val Gly Glu Thr Ala Arg Ala Asp His Val Gln Phe Asn Gly Tyr
                245                 250                 255

Gly Arg Glu Thr Phe Pro Gln Leu Ala Lys Val Asp Gly Leu Ala Asn
            260                 265                 270

Phe Ser Gln Val Thr Ser Cys Gly Thr Ser Thr Ala Tyr Ser Val Pro
        275                 280                 285

Cys Met Phe Ser Tyr Leu Gly Gln Asp Asp Tyr Asp Val Asp Thr Ala
        290                 295                 300

Lys Tyr Gln Glu Asn Val Leu Asp Thr Leu Asp Arg Leu Gly Val Gly
305                 310                 315                 320

Ile Leu Trp Arg Asp Asn Asn Ser Asp Ser Lys Gly Val Met Asp Lys
                325                 330                 335

Leu Pro Ala Thr Gln Tyr Phe Asp Tyr Lys Ser Ala Thr Asn Asn Thr
            340                 345                 350

Ile Cys Asn Thr Asn Pro Tyr Asn Glu Cys Arg Asp Val Gly Met Leu
        355                 360                 365

Val Gly Leu Asp Asp Tyr Val Ser Ala Asn Asn Gly Lys Asp Met Leu
        370                 375                 380

Ile Met Leu His Gln Met Gly Asn His Gly Pro Ala Tyr Phe Lys Arg
385                 390                 395                 400

Tyr Asp Glu Gln Phe Ala Lys Phe Thr Pro Val Cys Glu Gly Asn Glu
                405                 410                 415
```

```
Leu Ala Lys Cys Glu His Gln Ser Leu Ile Asn Ala Tyr Asp Asn Ala
            420                 425                 430

Leu Leu Ala Thr Asp Asp Phe Ile Ala Lys Ser Ile Asp Trp Leu Lys
        435                 440                 445

Thr His Glu Ala Asn Tyr Asp Val Ala Met Leu Tyr Val Ser Asp His
    450                 455                 460

Gly Glu Ser Leu Gly Glu Asn Gly Val Tyr Leu His Gly Met Pro Asn
465                 470                 475                 480

Ala Phe Ala Pro Lys Glu Gln Arg Ala Val Pro Ala Phe Phe Trp Ser
                485                 490                 495

Asn Asn Thr Thr Phe Lys Pro Thr Ala Ser Asp Thr Val Leu Thr His
            500                 505                 510

Asp Ala Ile Thr Pro Thr Leu Leu Lys Leu Phe Asp Val Thr Ala Gly
        515                 520                 525

Lys Val Lys Asp Arg Ala Ala Phe Ile Gln
    530                 535
```

<210> SEQ ID NO 3
<211> LENGTH: 34
<212> TYPE: DNA
<213> ORGANISM: Escherichia coli

<400> SEQUENCE: 3
tacttccaat ccaatgcaca gcatacttct gtgt                                34

<210> SEQ ID NO 4
<211> LENGTH: 37
<212> TYPE: DNA
<213> ORGANISM: Escherichia coli

<400> SEQUENCE: 4
tacttccaat ccaatgcaag tgcgccaaaa gatacca                             37

<210> SEQ ID NO 5
<211> LENGTH: 35
<212> TYPE: DNA
<213> ORGANISM: Escherichia coli

<400> SEQUENCE: 5
ttatccactt ccaatgttat tagcggatga atgcg                               35

<210> SEQ ID NO 6
<211> LENGTH: 47
<212> TYPE: DNA
<213> ORGANISM: Escherichia coli

<400> SEQUENCE: 6
tacttccaat ccaatgcaac atcacatcac tcttggtatc gctattc                  47

<210> SEQ ID NO 7
<211> LENGTH: 44
<212> TYPE: DNA
<213> ORGANISM: Escherichia coli

<400> SEQUENCE: 7
tacttccaat ccaatgcaac tgcgccaaca gacaccatct atca                     44

<210> SEQ ID NO 8
<211> LENGTH: 52
<212> TYPE: DNA
<213> ORGANISM: Escherichia coli -continued

```
<400> SEQUENCE: 8
ttatccactt ccaatgttat tactggataa atgccgcgcg gtctttgacc tt          52
```

ANTIBODIES FOR DETECTION OF COLISTIN-RESISTANCE

CROSS REFERENCE TO RELATED APPLICATION

This application claims priority to U.S. Provisional Patent Application Ser. No. 62/660,490, filed Apr. 20, 2018, the content of which is incorporated herein by reference in its entirety.

SEQUENCE LISTING

The Sequence Listing submitted via EFS-Web as ASCII compliant text file format (.txt) and filed on Mar. 14, 2019, named "SequenceListing_ST25," (created on Mar. 14, 2019, 11 KB), is incorporated herein by reference. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

FIELD OF THE INVENTION

The disclosed invention relates generally to novel antibodies and methods to detect bacterial proteins that confer multiple drug resistance. More particularly, the invention relates to high affinity monoclonal antibodies against proteins which confer resistance to colistin including variants thereof and associated methods of detecting the proteins.

BACKGROUND OF THE INVENTION

Antibiotics have been a critical public health tool since the discovery of penicillin in 1928, saving the lives of millions of people around the world. However, bacteria resistant to many antibiotics (i.e., multiple drug resistance) have emerged due to the extensive use of antibiotics in clinical settings, which creates numerous difficulties when treating bacterial infections. According to the Centers for Disease Control and Prevention (CDC), drug-resistant bacteria cause approximately 23,000 deaths and 2 million illnesses each year in the United States alone (see www.cdc.gov/drugresistance/index). Besides human health issues, antibiotic resistance also threatens animal health, agriculture, and the economy.

Colistin (also known as polymyxin E) is an antibiotic that is a mixture of the cyclic polypeptides colistin A and B and belongs to the class of polypeptide antibiotics known as polymyxins. It is not generally used to treat patients due to certain side effects; however, it has been found effective against certain kinds of multiple-drug resistant bacterial strains. In this capacity, it has great importance as a last-resort antibiotic to treat patients with multi-drug resistant infections. Resistance to colistin in human pathogens is generally rare but cases are being discovered more frequently. The first colistin-resistance gene in a plasmid which can be transferred between bacterial strains was found in 2011 in China and became publicly known in November 2015. The presence of this plasmid-borne gene (referred to as "mcr-1") was confirmed starting December 2015 in SE-Asia, several European countries and the United States (see e.g., Liu, Y. Y., et al., (2016). Lancet Infect Dis 16(2): 161-168).

The colistin-resistant bacterial strain was isolated from a pig and the mcr-1 gene responsible for the resistance was found to be plasmid-borne, capable of spreading from one type of bacterium to another. This was the first report for a transmissible colistin resistance determinant. Since then, the mcr-1 gene has been detected on at least four continents and in more than 20 countries. In the United States, for example, colistin-resistant strains have been isolated from patients in at least six states (see e.g., Castanheira, M., et al., (2016). Antimicrob Agents Chemother 60(9): 5623-5624; Kline, K. E., et al., (2016). MMWR Morb Mortal Wkly Rep 65(36): 977-978; McGann, P., et al., (2016). Antimicrob Agents Chemother 60(7): 4420-4421; Mediavilla, J. R., et al., (2016). MBio 7(4); Vasquez, A. M., et al., (2016). MMWR Morb Mortal Wkly Rep 65(36): 979-980; Meinersmann, R. J., et al., (2017). Antimicrob Agents Chemother 61(2)).

The colistin antibiotic acts by binding the lipid A component of lipopolysaccharides on the bacterial membrane and subsequently disrupting the bacterial membrane. The MCR-1 protein produced by bacteria is a phosphoethanolamine transferase that catalyzes the addition of phosphoethanolamine to lipid A to decrease binding of colistin to lipid A thereby reducing the antibiotic function of colistin (see e.g., Trent, M. S., et al., (2001). J Biol Chem 276(46): 43122-43131; Lee, H., et al., (2004). J Bacteriol 186(13): 4124-4133; Stojanoski, V., et al., (2016). BMC Biol 14(1): 81). The use of colistin is generally limited to treating severe infections caused by gram-negative bacteria in humans due to its toxicity (see e.g., Wertheim, H., et al., (2013). J Glob Antimicrob Resist 1(3): 131-134; Du, H., et al., (2016). Lancet Infect Dis 16(3): 287-288); however, it has been used extensively in veterinary medicine around the world to treat animal intestinal infections (see Catry, B., et al., (2015). Int J Antimicrob Agents 46(3): 297-306).

It is critical to timely screen for colistin resistance in patients and animals to prevent horizontal and clonal transmission as well as ensuring proper antibiotic selection for treatment. Currently, the only known method developed for rapid screening of colistin resistance is the polymerase chain reaction (PCR), which often has a high frequency of false-negative or unclear results due to the small sample volume and inhibitors present in biological samples (see e.g., Fach, P., et al., (2003). J Microbiol Methods 55(2): 383-392), and also a high frequency of false-positive results due to cryptic target gene sequences (such as free mcr plasmids or defective genes in bacteria) present in the samples or formation of PCR products from alternate DNA sequences (see e.g., Karch, H., et al., (1992). Infect Immun 60(8): 3464-3467; Bettelheim, K. A. & L. Beutin (2003). J Appl Microbiol 95(2): 205-217). In addition, a particular PCR protocol may miss some strains with mcr genes because of larger sequence variations among different mcr variants, such as mcr-2 (see e.g., Xavier, B. B., et al., (2016). Belgium. Euro Surveill 21(27)).

There thus exists an urgent need to address the deficiencies of the currently available capabilities and increase reliability and consistency for the identification of the presence of colistin-resistant bacteria, particularly those bacteria in patients, farm animals, and fresh produce, among other medical, agricultural, and industrial applications.

SUMMARY OF THE INVENTION

To address this urgent need, the present invention provides an increase in the current capabilities for the identification of colistin-resistant bacterial strains in various mediums. To complement the deficiency of existing methods (e.g., PCR), the present invention relates to the production and characterization of a collection of monoclonal antibodies specific to the colistin-resistant MCR proteins including variants thereof. The invention further relates to novel immunoassays using the collection of polyclonal and monoclonal antibodies to detect and confirm these proteins in different samples with a high degree of sensitivity and confidence.

In an aspect, the invention is a monoclonal antibody that reacts specifically with at least one MCR protein. The monoclonal antibody may be produced by a hybridoma cell line including cell lines having ATCC Patent Deposit Designation No. PTA-125013, ATCC Patent Deposit Designation No. PTA-125014, or a combination or coculture thereof. The monoclonal antibody may also be isolated and purified. In another aspect, the monoclonal antibody may include a label selected from the group consisting of: enzyme labels, radioisotopic labels, non-radioactive isotopic labels, chromogenic labels, fluorescent labels, chemiluminescent labels, and combinations thereof. In additional aspects of the invention, the monoclonal antibody may also be a component in a composition.

In another aspect, the invention is a method for detecting a protein which confers resistance to colistin. The method includes incubating a sample (e.g., aqueous, biological, environmental, fresh food, food product, processed food product, and combinations thereof) with a monoclonal antibody produced by a hybridoma cell line selected from the group consisting of ATCC Patent Deposit Designation No. PTA-125013, ATCC Patent Deposit Designation No. PTA-125014, and a combination or coculture thereof and detecting an immunological complex comprising the monoclonal antibody and the protein. The presence or absence of the immunological complex indicates the presence or absence of the protein in the sample. The immunological complex formed between the protein in the sample and the monoclonal antibody may also be isolated for further analysis. In aspects, the protein is selected from the group consisting of: MCR-1 protein having SEQ ID NO: 1; cMCR-1 protein having amino acid residues 214-541 of SEQ ID NO: 1; MCR-2 protein having SEQ ID NO: 2; cMCR-2 protein having amino acid residues 212-538 of SEQ ID NO: 2; recombinant versions of the foregoing; variants of the foregoing; and combinations thereof.

In a further aspect, the invention is a kit for detecting a protein in a sample (e.g., aqueous, biological, environmental, fresh food, food product, processed food product, and combinations thereof). The kit includes a container comprising a monoclonal antibody produced by a hybridoma cell line selected from the group consisting of: ATCC Patent Deposit Designation No. PTA-125013, ATCC Patent Deposit Designation No. PTA-125014, and a combination or coculture thereof as well as instructions for using the monoclonal antibody for the purpose of binding to the protein to form an immunological complex such that the presence or absence of the immunological complex indicates the presence or absence of the protein in the sample. The kit may also include a polyclonal antibody. In aspects, the protein is selected from the group consisting of: MCR-1 protein having SEQ ID NO: 1; cMCR-1 protein having amino acid residues 214-541 of SEQ ID NO: 1; MCR-2 protein having SEQ ID NO: 2; cMCR-2 protein having amino acid residues 212-538 of SEQ ID NO: 2; recombinant versions of the foregoing; variants of the foregoing; and combinations thereof.

It is an advantage of the present invention to provide a collection of novel monoclonal antibodies to detect and confirm the presence of MCR proteins and variants thereof with a high degree of sensitivity and confidence.

It is an additional advantage of the present invention to provide a collection of novel hybridoma cell lines that produce monoclonal antibodies to detect and confirm the presence of MCR proteins and variants thereof with a high degree of confidence.

Another advantage of the present invention is to provide methods of using the collection of novel antibodies either individually or in various combinations for diagnostic tests to detect the presence of MCR proteins and variants thereof in various samples such as those derived from animals, patients, the environment, and different stages of food production and processing.

A further advantage of the invention is to provide a kit for detecting MCR proteins and variants thereof in a sample.

This summary is provided to introduce a selection of concepts in a simplified form that are further described below in the detailed description. This summary is not intended to identify all key or essential features of the claimed subject matter, nor is it intended to limit the scope of the claimed subject matter.

STATEMENT OF DEPOSIT

Figure 1A:
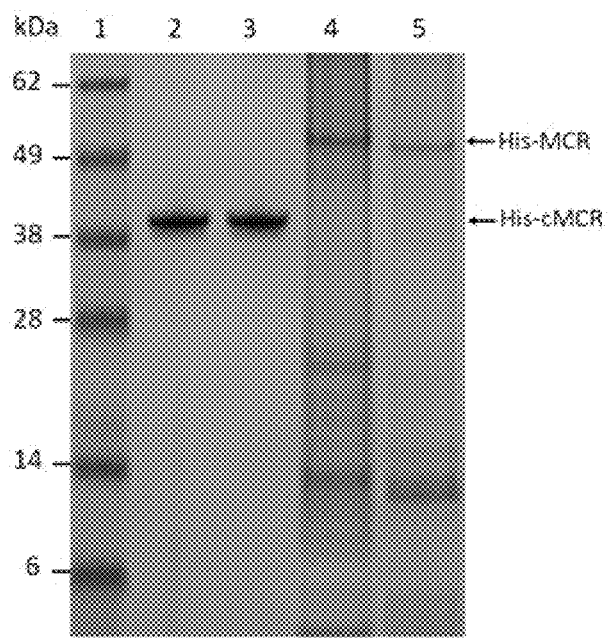
FIGS. 1A and 1B show analysis of His-tagged recombinant MCR-1 and MCR-2 proteins.

Monoclonal antibodies (mAb) to combined MCR proteins as expressed in the hybridoma cell lines described below were deposited on Feb. 28, 2018, with the American Tissue Culture Collection (ATCC®), P.O. Box 1549, Manassas, Va., 20108, USA. The mAb produced by the hybridoma cell line deposited under ATCC Patent Deposit Designation No. PTA-125013 recognizes MCR-1 protein. The mAb produced by the hybridoma cell line deposited under ATCC Patent Deposit Designation No. PTA-125014 recognizes MCR-1 protein.

These deposits have been made under the terms of the Budapest Treaty on the International Recognition of the Deposit of Microorganisms for the Purposes of Patent Procedure and the regulations thereunder. All restrictions on the availability to the public of these deposited hybridomas will be irrevocably removed upon issuance of a United States patent based on the present patent application. For the purposes of this invention, any hybridoma having the identifying characteristics of the deposited hybridomas including subcultures and variants thereof which have the identifying characteristics and activity as described herein are included within the scope of the invention.

The biological materials identified herein have been deposited under conditions such that access to the hybridomas are available during the pendency of the patent application to one determined by the Commissioner to be entitled thereto under 37 C.F.R. § 1.14 and 35 U.S.C § 122. The deposited biological material will be maintained with all the care necessary to keep them viable and uncontaminated for a period of at least five years after the most recent request for the furnishing of a sample of the deposited microorganism, and in any case, for a period of at least thirty (30) years after the date of deposit for the enforceable life of the patent, whichever period is longer.

We, the inventors for the invention described in this patent application, hereby declare further that all statements regarding this Deposit of the Biological Material made on information and belief are believed to be true and that all statements made on information and belief are believed to be true, and further that these statements are made with knowledge that willful false statements and the like so made are punishable by fine or imprisonment, or both, under section 1001 of Title 18 of the United States Code and that such willful false statements may jeopardize the validity of the instant patent application or any patent issuing thereon.

DETAILED DESCRIPTION OF THE INVENTION

Unless herein defined otherwise, all technical and scientific terms used herein generally have the same meaning as commonly understood by one of ordinary skill in the art to which this invention belongs. The definitions and terminology herein described for embodiments may or may not be used in capitalized as well as singular or plural form herein and are intended to be used as a guide for one of ordinary skill in the art to make and use the invention and are not intended to limit the scope of the claimed invention. Mention of trade names or commercial products herein is solely for the purpose of providing specific information or examples and does not imply recommendation or endorsement of such products.

As used in the description of the invention and the appended claims, the singular forms "a," "an," and "the" are intended to include the plural forms as well, unless the context clearly indicates otherwise.

As used herein, the term "about" refers to a quantity, level, value, or amount that varies by as much as 30%, preferably by as much as 20%, and more preferably by as much as 10% to a reference quantity, level, value, or amount. Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention.

The terms "antibody" (Ab) and/or "monoclonal antibody" (mAb) are known and recognized in the art and as used herein is meant to include intact molecules as well as fragments thereof (such as, for example, Fab and F(ab') sub.2 fragments) which are capable of binding MCR-1 and/or MCR-2 protein including variants thereof.

The term "catalytic domain" or "CD" is known and recognized in the art and means the part of the protein chain which contains the region where the catalyzed chemical reaction takes place. For example, the CD for MCR-1 protein (cMCR-1 protein) is amino acid residues 214-541 of the MCR-1 protein and the CD for MCR-2 protein (cMCR-2 protein) is amino acid residues 212-538 of the MCR-2 protein.

The term "chimeric" refers to antibodies modified to exhibit a desired biological activity (e.g., within humans or another species of animal such as livestock) having a portion of the heavy and/or light chain identical (i.e., homologous) to corresponding portions in antibodies derived from a particular species (e.g., belonging to a particular antibody class or subclass), while the remainder of the antibody is identical to corresponding sequences in antibodies derived from another species or belonging to another antibody class or subclass as well as fragments of such antibodies. It should be appreciated that the embodiments herein described may or may not include the use of a chimeric version of the antibodies used in the invention.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein). This term may be substituted for inclusive terms such as "comprising" or "including" to more narrowly define any of the disclosed embodiments or combinations/sub-combinations thereof. Furthermore, the exclusive term "consisting" is also understood to be substitutable for these inclusive terms in alternative forms of the disclosed embodiments.

The term "detecting the formation of the immunological complex" or the like is intended to include discovery of the presence or absence of MCR protein(s) in a sample. The presence or absence of such proteins can be detected using an immunoassay. A number of immunoassays used to detect and/or quantitate antigens are well known to those of ordinary skill in the art (see e.g., Harlow and Lane, Antibodies: A Laboratory Manual (Cold Spring Harbor Laboratory, New York 1988) 555-612). Such immunoassays include antibody capture assays, antigen capture assays, two-antibody sandwich assays, lateral flow immunoassays, and immunoaffinity assays. In an antibody capture assay, the antigen is attached to a solid support, and labeled antibody is allowed to bind. After washing, the assay is quantitated by measuring the amount of antibody retained on the solid support.

The term "effective amount" of a compound or property as provided herein is meant such amount as is capable of performing the function of the compound or property for which an effective amount is expressed. As is pointed out herein, the exact amount required will vary from process to process, depending on recognized variables such as the compounds employed and various internal and external conditions observed as would be interpreted by one of ordinary skill in the art. Thus, it is not possible to specify an exact "effective amount," though preferred ranges have been provided herein. An appropriate effective amount may be determined, however, by one of ordinary skill in the art using only routine experimentation.

The term "humanized" refers to a chimeric antibody (e.g., chimeric immunoglobulins, immunoglobulin chains, or fragments thereof) containing the amino acid sequence from the antigen-binding site of an antibody molecule of a parent or corresponding non-human mAb grafted onto a human antibody framework to confer desired immunologic properties and function within humans. Humanization of non-human antibodies is known in the art and commonly referred to as complementary determining region (CDR) grafting.

The term "isolated" or "isolated and purified" refers to material that is substantially or essentially free from components that normally accompany the referenced material in its native state.

The term "MCR protein" refers generally to any of the subtypes of proteins which confer resistance to colistin as disclosed herein including MCR-1 protein, recombinant MCR-1 protein, and their variants; MCR-1 CD protein, recombinant MCR-1 CD protein, and their variants; MCR-2 protein, recombinant MCR-2 protein, and their variants; MCR-2 CD protein, recombinant MCR-2 CD protein, and their variants; and combinations thereof. Specific reference is made herein to one or more of these subtypes and should be understood in the context of such reference.

The term "MCR-1 protein" means the phosphoethanolamine transferase which confers resistance to colistin having the amino acid sequence (541 amino acids in length) as indicated by SEQ ID NO: 1 based on the published GenBank® database sequence ASK04346.1.

The term "MCR-2 protein" means the phosphoethanolamine transferase which confers resistance to colistin having the amino acid sequence (538 amino acids in length) as indicated by SEQ ID NO: 2 based on the published GenBank database sequence WP_065419574.1.

The term "resistance to colistin" refers to bacteria that survive in the presence of colistin antibiotic due to the production of MCR-1 protein and variants thereof, MCR-2 protein and variants thereof, or both.

In embodiments, the present invention relates to monoclonal antibodies having specificity for MCR proteins and variants thereof. Described herein is the development and characterization of novel high-affinity monoclonal antibodies that specifically recognize these proteins as well as methods of using the antibodies to detect the presence of these proteins or the presence of bacteria that produce the proteins. The described antibodies are independent; however, some isotypes may have specificity for one or the other MCR protein subtype as discussed in the examples below. For those antibody isotypes with such specificity, no apparent cross-reaction was observed. For example, it was discovered that one mAb isotype recognized only MCR-1 proteins and two different mAb isotypes detected both MCR-1 and MCR-2 proteins. Of note is that these mAb isotypes can be of high value in different applications. The seven mAbs disclosed herein cross-reacting to both MCR-1 and MCR-2 proteins may be important resources for surveillance programs targeting a broad range of colistin-resistant bacteria from human and animals. The two MCR-1 protein specific mAbs disclosed herein could be useful for source-tracking of colistin-resistance among bacteria. These antibodies, and the assays that incorporate them, should therefore be just as effective at detecting any type of MCR protein subtype.

With respect to genetic conservation among mcr gene variants, the mcr-2 gene has about 77% nucleotide identity to mcr-1 and its gene product, MCR-2 protein, has about 81% amino acid sequence identity to MCR-1 protein. The identity levels of the N-terminal transmembrane domain and the C-terminal catalytic domain are approximately 72% and 87% between MCR-1 and MCR-2 proteins. Both MCR-1 and MCR-2 proteins account for bacterial resistance to colistin through catalyzing chemical modification of the LPS-lipid A moiety with addition of phosphoethanolamine to the phosphate group at the 4' position of the sugar (see e.g., Sun, J. et al. *MBio* 8, doi:10.1128/mBio.00625-17 (2017)). The invention disclosed herein is envisioned to be effective at detecting any variants of MCR proteins as well as the native MCR proteins.

In embodiments, the DNA coding for the soluble catalytic domain of MCR-1 protein is cloned into a bacterial expression vector and the recombinant MCR-1 protein is expressed in bacterial cells with a His tag. The MCR-1 protein is then purified using a Ni-NTA affinity column as further described herein. The His tag is then removed from the target protein using Tobacco Etch Virus (TEV) protease. The pure catalytic domain of the MCR-1 protein may be used as antigen for antibody production. For monoclonal antibody production, for example, female Balb/cJ mice are immunized at 2-week intervals by intraperitoneal injection of the target protein. Following cell fusion, hybridomas with desired antibody production are cloned. For polyclonal antibody production, for example, rabbits are immunized and sera is collected. Antibodies selected are typed and characterized for their binding specificity and sensitivity to recombinant cMCR-1 protein. It should be appreciated that any of the MCR protein subtypes described herein may be used as an antigen for antibody production by one of ordinary skill in the art. A sandwich enzyme-linked immunosorbant assay (ELISA) is established using the polyclonal antibody as a capture antibody and the monoclonal antibody with the highest ELISA reading in the direct as a detector. The sandwich ELISA for detection of MCR-1 protein produced by *E. coli* strains is described in the examples below as an exemplary embodiment. Other immunoassays such as portable lateral fluid devices may also be used for different application purposes as selected by a skilled artisan.

It should be appreciated that any classical or alternative methods may be used to prepare the antibodies of the invention as known to those of skill in the art. For instance, the monoclonal antibodies of the present invention can be prepared using classical cloning and cell fusion techniques. The immunogen (i.e., antigen) of interest (e.g., MCR-1 and/or MCR-2 proteins, the CD or other antigenic portions thereof, and variants thereof derived using DNA recombinant methods or separated subfragments) is typically administered (e.g. intraperitoneal injection) to wild-type mice or transgenic mice, rats, rabbits, or other animal species which can produce native, humanized, or other desired antibodies. The immunogen can be administered alone or as a fusion protein to induce an immune response with adjuvants known to one of skill in the art including, but not limited to oil-based adjuvants, such as Freunds adjuvant, synthetic adjuvants and aluminum salts. Fusion proteins comprise a peptide against which an immune response is desired coupled to a carrier protein, such as β-galactosidase, glutathione S-transferase, keyhole limpet hemocyanin (KLH), and bovine serum albumin, to name a few. In these cases, the peptides serve as haptens with the carrier proteins. After the animal is boosted, for example, three or four times, the spleen is removed and splenocytes are extracted and fused with myeloma cells using the well-known processes of Kohler and Milstein (Nature 256: 495-497 (1975)) and Harlow and Lane (Antibodies: A Laboratory Manual (Cold Spring Harbor Laboratory, New York 1988)). The resulting hybrid cells are then cloned in the conventional manner (e.g. using limiting dilution), screened and the resulting positive clones, which produce the desired monoclonal antibodies, are cultured.

Using the monoclonal antibodies of the invention in the format disclosed herein rapid detection of MCR proteins, including MCR-1 and/or MCR-2 proteins, as low as about 10 pg/mL in phosphate buffered saline (PBS) is possible implementing the methods of the invention. In embodiments, the assays herein described generally have a lower limit of detection (LOD) of about 0.01 ng/mL for MCR-1 protein and about 0.1 ng/mL for MCR-2 protein in buffer with coefficients of variation (CV) less than 15%. When applied to sampled such as ground beef, chicken, and pork, this ELISA was capable of identifying samples contaminated with less than 10 mcr-1 gene-carrying positive bacterial cells in 25 g of sample (e.g., at least about 0.4 colony forming unit per gram of sample), demonstrating its strong tolerance to complex food matrices (e.g., ground beef; ground pork; ground chicken; other meat products; agricultural products; samples derived from sources such as aqueous, biological, environmental, fresh food, food product, processed food product, and any combination thereof; the like; etc.; and all combinations of the foregoing). The dynamic range of detection may be optimized to be more narrow or broad depending on the application as determined by a skilled artisan. For example, lower detection limits for the method of the invention may be as low as about 10 bacterial cells/25 g meat in meat matrices. It should be appreciated, however, that an effective dynamic range is difficult to determine because inoculating 1 cell or 1000 cells in meat samples may lead to a similar result. The bacterial cells starting 1 or 1000 will reach stationary phase, then enter death phase after overnight culture, and the detection of MCR proteins is based on the numbers of bacterial cells. The results generally showed that no false positive/negative results were obtained using overnight culture.

An embodiment of the invention is the use of the sandwich ELISA to detect any of the MCR protein subtypes from a sample with minimal sample preparation or modification using either one of disclosed mAb or any combination of the mAbs with or without a polyclonal antibody. The particular conditions for the ELISA will be determined by one of ordinary skill in the art. In embodiments, one or more of the mAb herein disclosed is used for a diagnostic screening to test and confirm the presence of colistin resistant bacterial strains in a variety of samples such as, for example, aqueous, biological, environmental, fresh food, food product, processed food product, meats, dairy, fruits, vegetables, etc., the like, and combinations thereof.

Antibodies, or fragments thereof, may be labeled using any of a variety of labels and methods of labeling known to those of skill in the art. Examples of types of labels which can be used in the present invention include, but are not limited to, enzyme or enzymatic labels, radioisotopic labels, non-radioactive isotopic labels, chromogenic labels, fluorescent labels, and chemiluminescent labels (see e.g., Harlow and Lane, Antibodies: A Laboratory Manual [Cold Spring Harbor Laboratory, New York 1988] 555-612).

In further embodiments, methods for detecting MCR proteins in a sample containing such proteins includes contacting the sample with an antibody by binding to a capture antibody which is then detected with the detector antibody. The detector antibody can be directly labeled with enzymes, fluorophores, etc. and thus is directly detected. The detector antibody in the present assay can be labeled using any label known in the art.

A variation of this assay is a competitive ELISA—as represented by at least one embodiment of the invention—wherein the antigen is bound to the solid support and two solutions containing antibodies which bind the antigen from a sample and a monoclonal antibody of the present invention compete for binding of the antigen. The amount of monoclonal antibody bound is then measured, and a determination is made whether the sample contains MCR protein wherein detection of large amounts of monoclonal antibody bound to the coated antigen indicates a small to no MCR protein presence in the sample.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen. These immunoassays typically rely on labeled antigens, antibodies, or secondary reagents for detection. These proteins can be labeled with radioactive compounds, enzymes, biotin, fluorochromes, other labels known in the art, and the like. Of these, radioactive labeling is most common and can be used for almost all types of assays and with most variations.

Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1-31), Schurs, A. H. W. M., et al. 1977 (Clin. Chim Acta 81:1-40), Bobrovnik, S. A. 2003 (J. Biochem. Biochys. Methods 57:213-236), and Friguet et al 1985 (J. Immunol. Methods 77:305-319).

Examples of suitable enzyme labels include malate hydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^{3}$H, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc.

Examples of suitable fluorescent labels include a $^{152}$Eu label, a fluorescein label, an isothiocyanate label, a rhodamine label, a phycoerythrin label, a phycocyanin label, an allophycocyanin label, an o-phthaldehyde label, a fluorescamine label, etc.

Examples of chemiluminescent substrates include a luminal substrate, an isoluminal substrate, an aromatic acridinium ester substrate, an imidazole substrate, an acridinium salt substrate, an oxalate ester label, a luciferin substrate, a luciferase label, an aequorin label, etc.

In embodiments, the invention also provides kits which are useful for carrying out detection methods of the present invention. The kit includes a container comprising a monoclonal antibody produced by at least one hybridoma cell line of the present invention and instructions for using the monoclonal antibody for the purpose of binding to the proteins to form an immunological complex such that the presence or absence of the immunological complex correlates with or indicates the presence or absence of the proteins in the sample. The kits can comprise a first container means containing the antibodies described herein. The kit can also comprise other container means having solutions necessary or convenient for carrying out the invention. The container means can be made of glass, plastic, foil, the like, and combinations thereof and can be any suitable vial, bottle, pouch, tube, bag, box, etc. The kit can also contain written information, such as procedures for carrying out the present invention or analytical information, such as the amount of reagent contained in the first container means. The container means can be in another container means (e.g., a box, bag, etc.) along with the written information.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement. The following examples are intended only to further illustrate the invention and are not intended in any way to limit the scope of the invention as defined by the claims.

Materials and Methods

Ethics Statement. All procedures with animals were carried out according to institutional guidelines for husbandry (USDA ARS Directive #130.4.v.3) and specific procedures and protocols for antibody production were reviewed and approved by the Western Regional Research Center (WRRC) Institutional Animal Care and Use Committee (IACUC).

Bacterial Strains. Escherichia coli (E. coli) strains (AR-Bank #0346 and AR-Bank #0349—kindly provided by FDA-CDC Antimicrobial Resistance Bank, Atlanta, Ga.) were used as positive controls for plasmid encoded mcr-1 gene (see e.g., Hasman, H., et al., 2015, Euro Surveill 20(49)). These positive-control strains harbored the mcr-1 gene on a multicopy plasmid. An E. coli strain having accession number ATCC 25922 (serotype 06) and ATCC 29425 (serotype K12) were purchased from ATCC and used as negative controls.

Construction, Expression, and Purification of MCR recombinant proteins from Bacterial Strains. Genes encoding the full-length MCR-1 protein (SEQ ID NO: 1) and the catalytic domain of the MCR-1 protein (cMCR-1: amino acid residues 214-541 of SEQ ID NO: 1) were amplified by PCR using the plasmid pBSKSII-KanR-mcr1 (kindly provided by Dr. Timothy Plazkill, Baylor College of Medicine, Houston, Tex. 77030) as a template and forward primers having SEQ ID NO:3 (for the full-length mcr-1 gene), SEQ ID NO:4 (for the catalytic domain of the mcr-1 gene) and SEQ ID NO:5 as the reverse primer. Genes coding for the full length MCR-2 protein (SEQ ID NO: 2), and the catalytic domain of the MCR-2 protein (cMCR-2: amino acid residues 212-538 of SEQ ID NO: 2) were amplified by PCR using the mcr-2 gene synthesized by Integrated DNA Technologies, Inc. (Coralville, Iowa: www.idtdna.com) based on the published GenBank sequence (NG_051171.1) as a template and forward primers having SEQ ID NO: 6 (for the full-length mcr-2 gene), SEQ ID NO: 7 (for the catalytic domain of the mcr-2 gene), and reverse primer SEQ ID NO: 8.

Expression of Recombinant Proteins. PCR products were inserted into the vector pET His6 TEV LIC cloning vector (1B) (Addgene, Cambridge, Mass., plasmid #29653). The four constructs encoding recombinant MCR-1 and MCR-2 proteins were constructed, expressed, and the proteins were purified from E. coli bacterial strains. All the constructs encoding MCR-1 and MCR-2 proteins had 6×His tag at the N-terminus and were expressed in competent BL21DE3 E. coli cells. An overnight culture (20 mL) was used to inoculate 1 L of LB medium supplemented with 50 μg/mL of kanamycin. The cell culture was then incubated at 37° C. with shaking until it reached an $OD_{600}$ of 0.6. Expression of the recombinant proteins was induced for 20 hours at 16° C. with isopropyl β-D-1-thiogalactopyranoside (IPTG) with 1 mM final concentration. Cells were harvested by centrifugation at 8,000 rpm for 30 min at 4° C. The cell pellet was then resuspended in buffer A (200 mM NaCl, 20 mM Tris pH 8, 20 mM Imidazole pH8), which was supplemented with protease inhibitors (P8849, Sigma-Aldrich, St. Louis, M063178) and DNase (10 ng/mL, Sigma-Aldrich, Product: 4716728001). For cells carrying the full-length MCR-1 and MCR-2 proteins, the cell pellet was resuspended in buffer A plus 0.01% Triton-100, and for cells carrying the cMCR proteins, the cell pellet was resuspended in buffer A without adding 0.01% Triton-100 (because cMCR proteins are soluble, but full-length MCR proteins are not water soluble). Cells were ruptured by sonication. Whole lysate was centrifuged for 1 hour at 15,000 rpm and the supernatant was loaded onto a 5-mL HisTrap FF Crude column (GE Healthcare, Piscataway, N.J.), washed with five bed volumes of buffer A, and the proteins were eluted with buffer A supplemented with 300 mM imidazole, pH8. cMCR-1 and cMCR-2 proteins were further purified by size-exclusion chromatography (SEC) using Superdex 200—XK 26/70 column (GE Healthcare). For the cMCR-1 protein, the N-terminal His-tag was removed by tobacco etch virus (TEV) protease before gel filtration. Protein concentration was determined by absorbance measurements at 280 nm using an absorbance coefficient (0.1%) of 1.03 for cMCR-1 and 1.12 for cMCR-2 (ProtParam tool: www.expasy.org/tools). Mass spectrometry for verification of the full-length recombinant MCR-1 protein was performed by UC Berkeley, Vincent J. Coates Proteomics/Mass Spectrometry Laboratory (http://qb3.berkeley.edu/pmsl/).

Polyclonal Antibody (pAb) Production. Production of polyclonal antibodies recognizing MCR-1 protein was performed by Pacific Immunology Corp (Ramona, Calif.) as previously described (see e.g., He, X., et al., (2013). J Immunol Methods 389(1-2): 18-28). Briefly, two rabbits were used and each rabbit was injected with 300 μg of cMCR-1 protein at 3-week intervals for a total of four injections. Bleeds were collected and evaluated for their binding to cMCR-1 protein by direct ELISA with 10 ng/mL of cMCR-1 protein in phosphate buffered saline (PBS) as the plate-coating antigen. Antibodies were purified using Protein-A affinity column (Pierce, Rockfield, Ill.). Purified IgG concentration was determined by absorbance measurement at 280 nm using the Eppendorf BioSpectrometer (Eppendorf, Hauppauge, N.Y.) and absorbance coefficient (0.1%) of 1.36.

Cell Culture Media. Hybridoma medium (HM) consisted of Iscove's modified Dulbecco's Minimal Medium (Sigma-Aldrich Corp., St. Louis, Mo., Product #1-7633) containing $NaHCO_3$ (36 mM), and glutamine (2 mM). All hybridomas and SP2/0 mouse myeloma cells were maintained in HM supplemented with 10% fetal calf serum (cHM). Hybridomas were selected following cell fusion using HAT selection medium prepared by adding hypoxanthine (5 μM), aminopterin (0.2 μM), and thymidine (0.8 μM) to cHM. Macrophage conditioned medium (MPCM) was prepared as described (see e.g., Sugasawara, R. J. et al., (1985). J Immunol Methods 79(2): 263-275). A mixture of cHM and 40% MPCM was used for all cell-cloning procedures.

Fusion Procedure. Three days following the last IP injection mice were euthanized and their splenocytes were fused with SP2/0 myeloma cells using polyethylene glycol as previously described (see e.g., Bigbee, W. L., et al., (1983), Mol Immunol 20(12): 1353-1362). Following cell fusion, the fused cells were suspended in 100 mL of HAT selection medium supplemented with 10% fetal calf serum and 10% MPCM, dispensed into ten 96-well tissue culture plates, and incubated for 10 to 14 days at 37° C. in 5% $CO_2$ before screening for antibody production.

Monoclonal Antibody Production and Purification. Monoclonal antibodies (mAbs) were prepared and screened as described previously (see e.g., He, X. et al., *J Immunol Methods* 389, 18-28, doi:10.1016/j.jim.2012.12.005 (2013)). Briefly, female Balb/cJ mice (Simonsen Laboratories, Gilroy, Calif.) were immunized at 2-week intervals by intraperitoneal injection (IP) of 100 µL of recombinant cMCR-1 (50 µg/mL) protein in Sigma Adjuvant System (Sigma, St. Louis, Mo.). Following the third injection, sera were obtained (50 µL/mouse) and evaluated for anti-MCR-1 titers. Mice with a strong antibody titer were boosted with a fourth IP injection two weeks after the third injection with a single dose of cMCR-1 protein (100 µL at 10 µg/mL in PBS without adjuvant). Three days later, mice were euthanized and their splenocytes were fused with SP2/0 myeloma cells using polyethylene glycol as previously described (see e.g., Bigbee, W. L., et al., *Mol Immunol* 20, 1353-1362 (1983)). The culture media of hybridomas were screened with a direct ELISA using 0.1 µg/mL of cMCR-1 in PBS as the plate-coating antigen. The positive cell cultures were cloned 3-4 times by limiting dilution until selected hybridomas were clonal. Selected hybridomas were then expanded and antibodies were purified from culture supernatant by affinity chromatography using a Protein-G conjugated Sepharose column (Sigma, #P-32196) and bound antibodies were eluted with 0.1 M glycine-HCl, pH 2.7. Purified IgG concentration was determined by absorbance measurement at 280 nm using the Eppendorf BioSpectrometer (Eppendorf, Hauppauge, N.Y.) and absorbance coefficient (0.1%) of 1.36. Antibody isotype was determined by ELISA using cMCR-1 protein-coated microtiter plates and horseradish peroxidase (HRP)-conjugated, isotype-specific antibodies (SouthernBiotech, Birmingham, Ala.).

Enzyme-Linked Immunosorbent Assay (ELISA). Direct ELISAs were performed by directly coating variable amounts of cMCR-1 protein in wells of black NUNC plates (Thermo Fisher Scientific, Waltham, Mass.) and incubating overnight at 4° C. Plates were then blocked with a blocking buffer [BB: 5% non-fat dry milk (NFDM) in 0.02M Tris-buffered saline with 0.9% NaCl, pH 7.4 and 0.05% Tween-20 (TBST)] for 1 hour at room temperature (RT). Different mAbs (1 µg/mL in BB) were added to the plates and incubated for 1 hour at RT after washing two times with TBST. After washing six times with TBST, the plates were incubated with goat anti-mouse IgG conjugated with HRP (GAM-IgG-HRP, Promega, Madison, Wis., 200 ng/mL in BB) for 1 hour at RT. SuperSignal West Pico Chemiluminescent Substrate (Pierce) was then added and luminescence counts were measured in counts per second (cps) using the Victor-3 plate reader (Perkin-Elmer, Shelton, Conn.). The procedures and reagents used for the sandwich ELISAs were similar to the direct ELISA described except that the plates were first coated with the rabbit pAb against the cMCR-1 protein (1 µg/mL in PBS), and then the MCR-1 proteins were added. The detection antibody was mAb MCR-7 (100 ng/mL in BB). ELISA limit of detection (LOD) was determined using the lowest concentration of analyte that generated a response greater than the background plus three times the standard deviation. For each ELISA test, three independent experiments in triplicate were performed and one representative data set is presented. Statistical significance was determined by two-tailed unpaired Student's t-test ($p<0.05$ was considered significant). ELISA standard curves were generated using GraphPad Prism 6 (GraphPad Software, La Jolla, Calif.). ELISA intra-day precision was determined based on results obtained from two independent assay runs within a day. Three replicates were analyzed for each concentration at each run. The % CV for each concentration was calculated by dividing the standard deviation (SD) by mean ELISA readings calculated from two runs (total 6 replicates), and multiplying by 100. The inter-day precision (% CV) was determined by dividing the SD of 3 day means by mean of 3 day means, and multiplying by 100.

Polyacrylamide Gel Electrophoresis (PAGE) and Western Blot. All gel electrophoresis equipment, buffers, gels and polyvinylidene difluoride (PVDF) membranes were purchased from Invitrogen (Thermo Fisher Scientific). MCR-specificity of each mAb was analyzed by Western blot. Protein samples were separated by SDS-PAGE using 4-12% NuPAGE (denatured) Novex Bis-Tris mini gels following the manufacturer's protocol. To visualize proteins directly after gel electrophoresis, 2 µg of the protein of interest was loaded in each lane and gels were stained with SimplyBlue SafeStain (Thermo Fisher Scientific). For Western blot analysis, 0.2-0.5 µg/lane of protein was loaded and separated by SDS-PAGE. Proteins were electronically transferred to PVDF membranes (0.45 um). The membranes were blocked with 5% NFDM, then probed with mAbs (500 ng/mL), followed by GAM-IgG-HRP (25 ng/mL). Bound antibody was detected using the Amersham ECL-Plus Western Blotting Detection System (GE Healthcare, UK) according to manufacturer's protocol.

Detection of MCR-1 Protein in Meat Samples. Meat samples, including ground beef, chicken, and pork were purchased from a local supermarket and packed into stomacher bags (Seward Stomacher 400 Classic Filter Bags, Nelson Jameson Inc., Marshfield, Wis.), 25 g/bag. Samples were kept at 4° C. before use. Inocula of *E. coli* strains were created by serially diluting an overnight axenic culture from frozen stock, shaken and grown at 37° C., into buffered peptone water (BPW), to a desired cfu/mL of 10 cfu per 25 g (or mL) of sample. Actual inoculum levels were later determined via spread-plating 0.1 mL of cultures onto tryptic soy agar (TSA) plates and incubating overnight at 37° C. One mL of the prepared dilutions or BPW control was added to the samples. Enrichment broth, 75 mL of tryptic soy broth (TSB) with colistin (2 µg/mL), was then added to dilute 25 g (or mL) of each sample, and the sample-broth solution was mixed by hand-massaging. Enrichment was then performed in a growth chamber for 16 hours at 37° C. with shaking (100 rpm). Post enrichment, 1 mL sample aliquots were removed from the Stomacher bags and pipetted into microcentrifuge tubes. After centrifugation, bacterial cell pellets were lysed with 1 mL B-PER containing protease inhibitors (P8849, Sigma-Aldrich) and DNase (10 ng/mL, Sigma-Aldrich, Product: 4716728001). A portion (100 µL) of each sample aliquot was added to the ELISA microtiter wells for ELISA test.

Results and Discussion

Figure 1B:
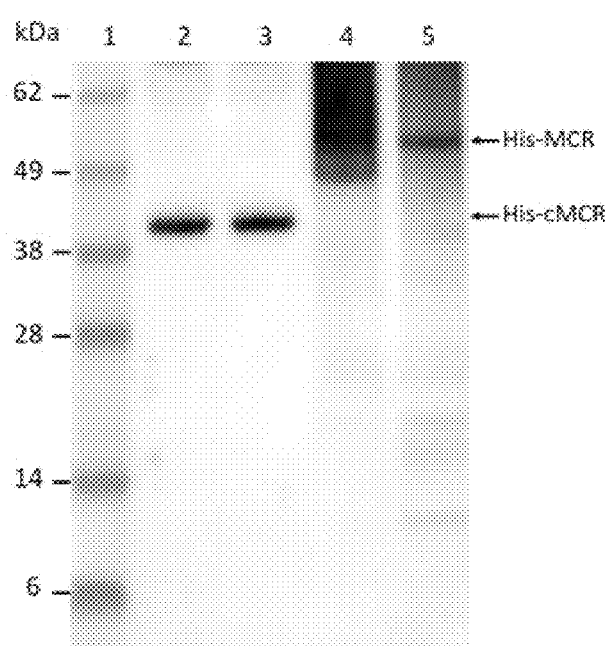
Figure 2A:
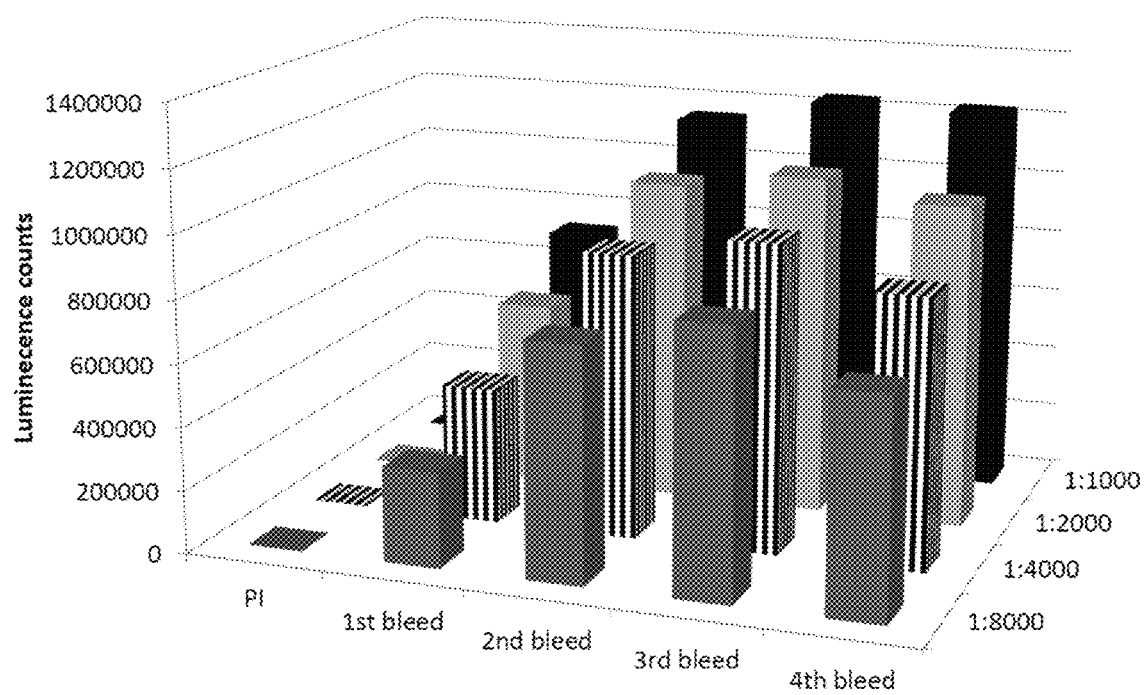
FIG. 2A shows activity of polyclonal antibodies from immunized rabbit serum to MCR-1 protein.

Generation of Standard for MCR Protein Assays. FIGS. 1A and 1B show analysis of His-tagged recombinant MCR-1 and MCR-2 proteins. FIG. 1A shows SDS-PAGE of partially purified MCR recombinant proteins stained with SimplyBlue: lane 1, Protein markers with molecular weights (kDa) indicated at the left; lane 2, cMCR-1; lane 3, cMCR-2; lane 4, MCR-1; lane 5, MCR-2. FIG. 2A shows Western blot analysis of partially purified MCR recombinant proteins using anti-His antibody: lane 1, Protein markers with molecular weights (kDa) indicated at the left; lane 2, cMCR-1; lane 3, cMCR-2; lane 4, MCR-1; lane 5, MCR-2. The predicted His-MCR (full-length) and His-cMCR (catalytic domain) protein bands are indicated by arrows at the right. Full-length recombinant MCR-1 and MCR-2 proteins with an N-terminal $His_6$-tag sequence were expressed in E. coli BL21 DE3 cells and purified using a HisTrap FF column as discussed above. The predicted molecular weights of the $His_6$-MCR-1 and $His_6$-MCR-2 is ~61 kDa based on GenBank sequences (ASK04346.1 and WP_065419574.1), but the size revealed on SDS-PAGE and Western blots looked slightly smaller than 61 kDa (FIGS. 1A and 1B). To confirm the intactness of the protein, mass spectrometry (MS) was performed. The N-terminal His-tagged full-length MCR-1 was digested with trypsin and chymotrypsin. The peptides obtained from two proteases covered 60.6% of the MCR-1 sequence (data not shown). This result suggests that the intact MCR-1 was recovered from E. coli. The failure to identify the N-terminal 100 amino acids by MS might be due to intrinsic hydrophobicity that MCR consists of one membrane-spanning domain (residues 1-214), one soluble catalytic domain (residues 215-541), and sufficient amounts of soluble catalytic domain have been produced in E. coli (see e.g., Liu et al., Lancet Infect Dis 16, 161-168, doi:10.1016/S1473-3099(15)00424-7 (2016)). Therefore, the C-terminal periplasmic catalytic domains of MCR-1 protein (cMCR-1, residues 214-541) and MCR-2 protein (cMCR-2, residues 212-538) were produced in E. coli and purified by HisTrap FF chromatography followed by gel filtration. The resulting protein preparations yielded one band with molecular weight close to the expected size of His-cMCR, 38.4 kDa (FIGS. 1A and 1B). These preparations were used as standards for the immunoassays of MCR-1 and MCR-2 described below.

Figure 2B:
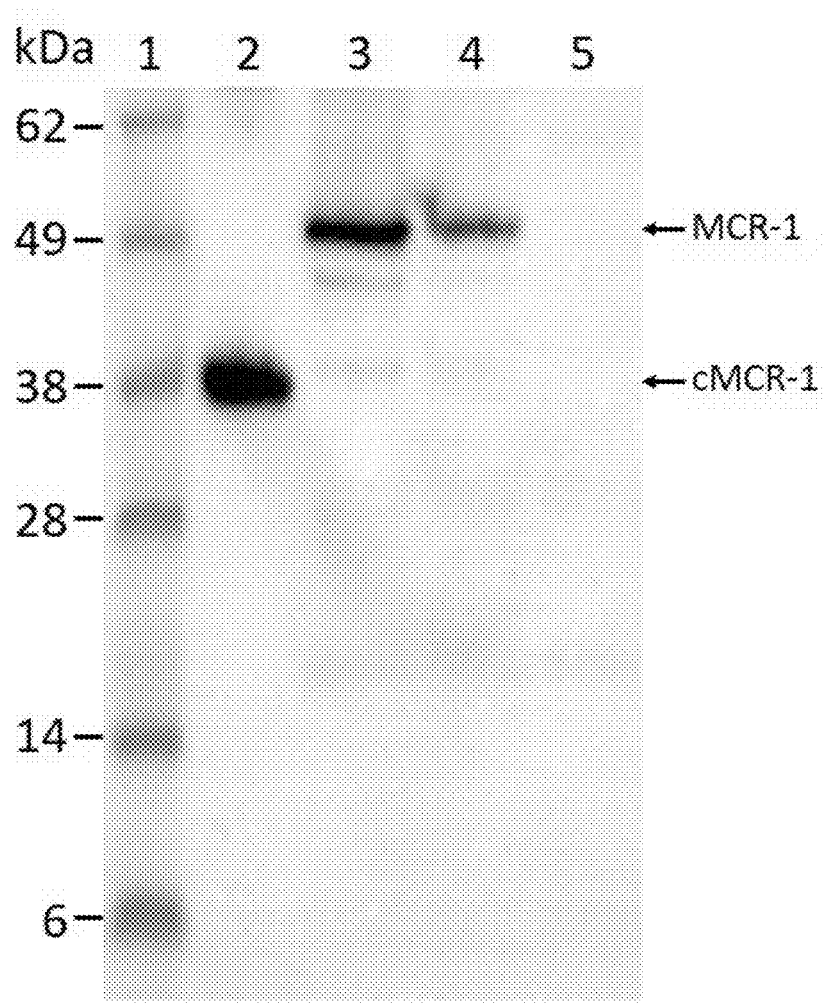
FIG. 2B illustrates the reactivity of immunized rabbit serum IgG to MCR-1 protein determined by Western blot.

Development and Characterization of Polyclonal Antibodies Against MCR Proteins. To develop polyclonal antibodies that bind specifically to MCR proteins, the recombinant catalytic domain, cMCR-1 (residues 214-541) with His-tag removed, was used as an immunogen for antibody production as discussed above. The polyclonal antibodies (pAb) made in two rabbits had high antibody serum titers (≥1:8,000). FIG. 2A shows the ELISA results from one of the two rabbits immunized with the cMCR-1. ELISA analysis of antisera from pre-immune (PI), 1st bleeding, 2nd bleeding, 3rd bleeding, and 4th bleeding is shown in FIG. 2A. ELISA was performed by directly coating cMCR-1 (10 ng/mL) on the plate, then using antisera of rabbit #1 diluted in a range of 1:1,000-1:8,000 as a detection antibody and goat anti-rabbit-IgG HRP conjugate (200 ng/mL) as a secondary antibody. Each column represents the mean of 3 independent repeats performed in duplicates, the standard deviation for each column ranges from 7 to 51654. The $1^{st}$, $2^{nd}$, $3^{rd}$, and $4^{th}$ bleed from two immunized rabbits were then pooled and used to purify IgG for further experimentation. The IgG purified from the pooled pAb bound to the recombinant cMCR-1 (with His-tag removed). It also bound to a protein with size similar to the full-length recombinant MCR-1 in cell lysates of mcr-1 positive strains, AR-Bank #346 and AR-Bank #349, but not in cell lysate of mcr-1 negative strain, ATCC25922, as demonstrated by Western blot analysis (FIG. 2B). FIG. 2B illustrates the reactivity of immunized rabbit serum IgG to MCR-1 determined by Western blot. Lane 1, Protein markers with molecular weights (kDa) indicated at the left; Lane 2, Purified cMCR-1 (0.5 µg); Lanes 3 to 5, Cell lysates from bacterial strains AR-Bank #346, AR-Bank #349, and ATCC25922 (colistin negative strain) respectively. Samples were separated by SDS-PAGE under non-reducing conditions. The expected sizes of the recombinant MCR-1 catalytic domain and full-length MCR-1 produced by wild type bacteria are indicated at the right side of the blot. These results suggest that the pAb is specific for the MCR-1.

Figure 3:
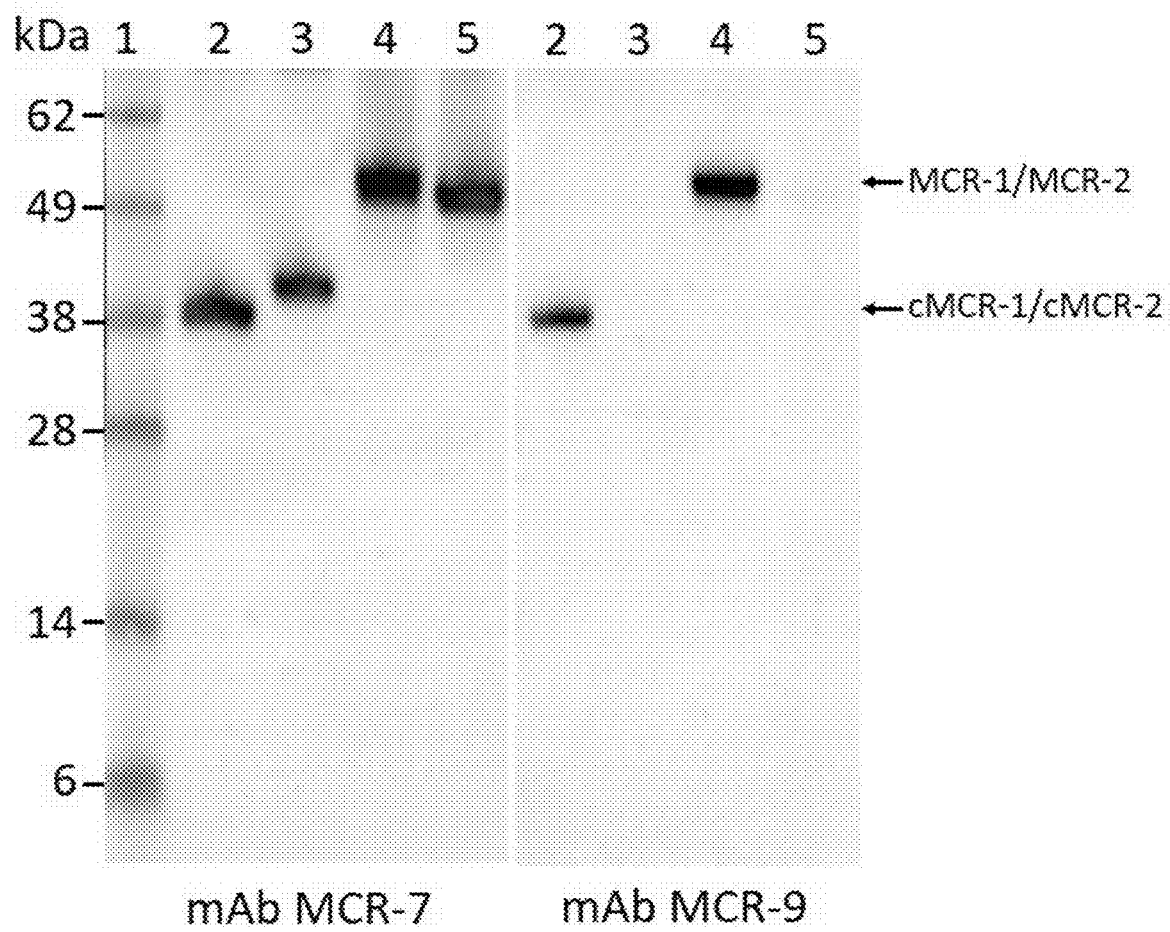
FIG. 3 illustrates Western blot analysis of mAb reactivity to MCR-1 and MCR-2 proteins with the indicated mAbs.
Figure 4:
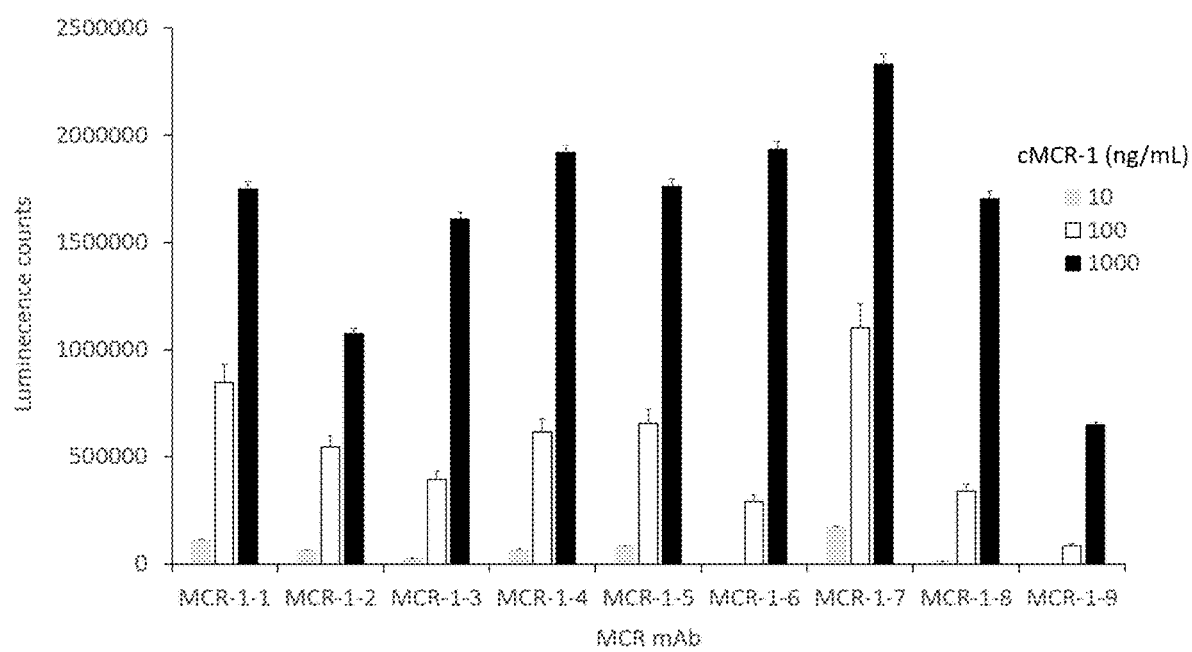
FIG. 4 illustrates binding affinity of nine mAbs evaluated by a direct ELISA, in which each MCR mAb was allowed to react with the purified cMCR-1 protein.

Development and Characterization of Monoclonal Antibodies Against MCR Proteins. To develop monoclonal antibodies that bind specifically to MCR proteins, the recombinant catalytic domain, cMCR-1 (residues 214-541) with His-tag removed, was used as an immunogen for antibody production as discussed above. For mAb production and identification, 1,000 culture wells following splenocyte-myeloma cell fusion were screened. Nine cell lines were selected for further investigation based on their antibody yields and ELISA titers. The mAbs produced by these cell lines were designated as mAb MCR-1 through mAb MCR-9. ELISA isotyping study indicated that the mAbs were predominantly IgG1, except for mAb MCR-7, which has an IgG2b type heavy chain. All of the mAbs possessed kappa light-chains (Table 1). To determine the reactivity of each mAb to MCR-1 protein and MCR-2 protein, recombinant MCR-1 and MCR-2 catalytic domains and full-length proteins were analyzed by Western blot analyses following SDS-PAGE. FIG. 3 demonstrates that mAb MCR-1-7 binds to both MCR-1 and MCR-2, while mAb MCR-1-9 binds only to MCR-1, suggesting that mAb MCR-1-7 recognizes an epitope that is highly homologous in MCR-1 and MCR-2. FIG. 3 illustrates Western blot analysis of mAb reactivity to MCR-1 and MCR-2. Lane 1, Protein markers with molecular weights (kDa) indicated at the left; Lane 2, Purified cMCR-1 with His-tag removed (0.2 µg); Lane 3, Purified cMCR-2 with His-tag on (0.2 µg); Lanes 4 and 5, Purified His-full-length MCR-1 and His-full-length MCR-2. Blots were probed with indicated mAbs following SDS-PAGE under non-reducing condition. The expected sizes MCR-1 and MCR-2 proteins are indicated at the right side of the blot In contrast, the epitope recognized by mAb MCR-1-9 resides in a region of structural difference between MCR-1 and MCR-2. The specificity of all nine mAbs for MCR-1 and MCR-2 proteins is summarized in Table 1. These antibodies could prove valuable in a variety of applications. The seven mAbs cross-reacting with MCR-1 and MCR-2 proteins are important resources for surveillance programs targeting a broad range of colistin-resistant bacteria from human and animals. The two MCR-1 protein specific mAbs could be useful for source-tracking purposes. The binding affinity of nine mAbs was evaluated by a direct ELISA, in which each MCR mAb was allowed to react with the purified cMCR-1 protein directly coated onto microplates in phosphate-buffered saline (PBS). FIG. 4 illustrates that the ELISA value for mAb MCR-1-7 is significantly higher than those for the other mAbs (p≤0.01). FIG. 4 illustrates detection of cMCR-1 by direct ELISA using nine different mAbs. cMCR-1 (10-1,000 ng/mL) was directly coated onto microtiter wells and then incubated with mAbs at 1 µg/mL. Data represent the mean of triplicate plus standard deviation.

TABLE 1

| Antibody | Isotype | Specificity |
|---|---|---|
| MCR-1-1 | IgG1, kappa | MCR-1, MCR-2 |
| MCR-1-2 | IgG1, kappa | MCR-1, MCR-2 |
| MCR-1-3 | IgG1, kappa | MCR-1, MCR-2 |
| MCR-1-4 | IgG1, kappa | MCR-1 |
| MCR-1-5 | IgG1, kappa | MCR-1, MCR-2 |
| MCR-1-6 | IgG1, kappa | MCR-1 |
| MCR-1-7 | IgG2b, kappa | MCR-1, MCR-2 |
| MCR-1-8 | IgG1, kappa | MCR-1, MCR-2 |
| MCR-1-9 | IgG1, kappa | MCR-1 |

Figure 5A:
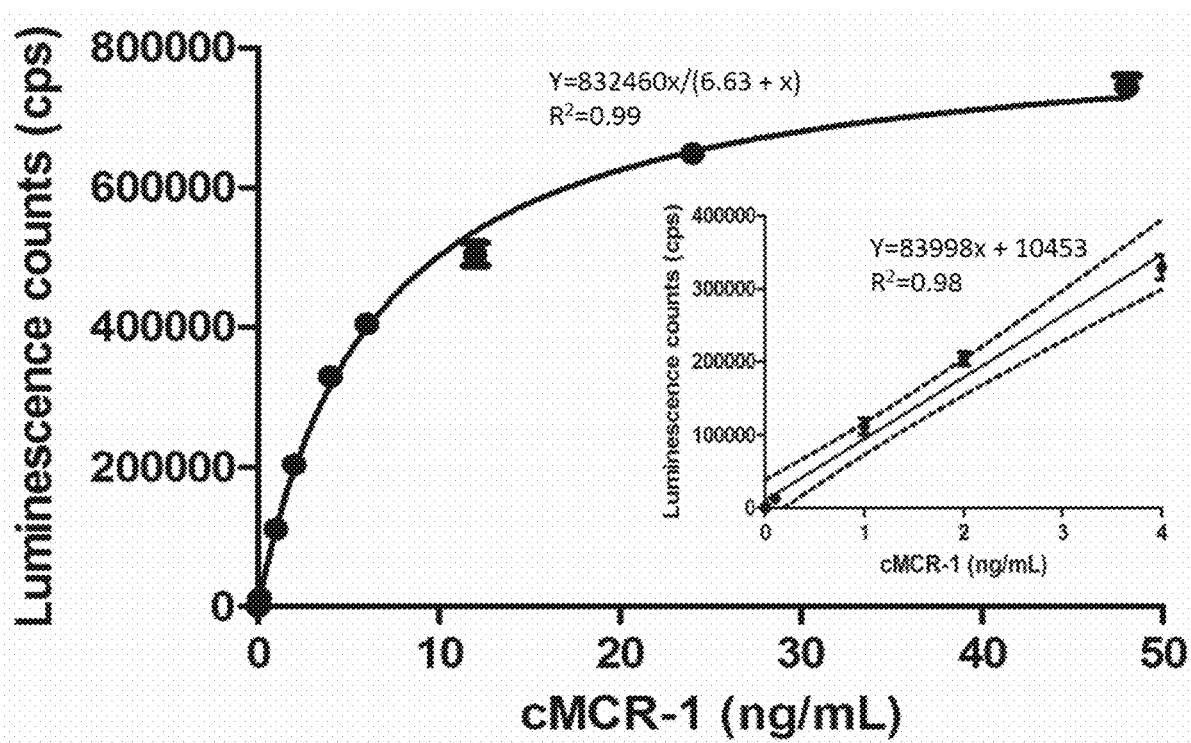
FIG. 5A depicts the detection of the cMCR-1 protein using the sandwich ELISA based on the pAb-mAb-MCR-1-7 configuration.
Figure 5B:
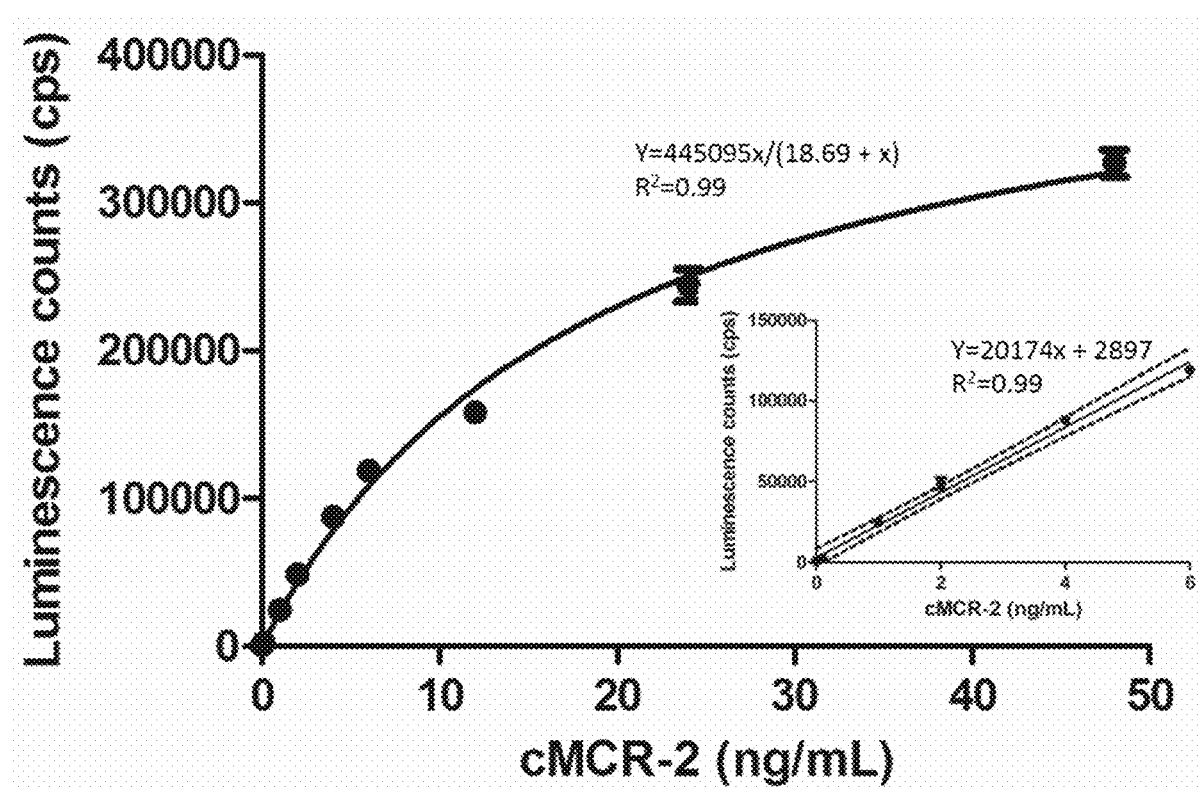
FIG. 5B depicts the detection of the cMCR-2 protein using the sandwich ELISA based on the pAb-mAb-MCR-1-7 configuration.

Sensitivity, Specificity, and Linearity of Sandwich ELISA for cMCR-1 and cMCR-2. To develop a sensitive sandwich ELISA for MCR proteins, each mAb was evaluated for its performance as a detection antibody by using the pAb as capture antibody (data not shown). In agreement with results obtained from the direct ELISA and Western blot analysis, mAb MCR-1-7 not only generated the highest ELISA signal among all mAbs tested, but also detected both cMCR-1 and cMCR-2 in the sandwich ELISA. FIGS. 5A and 5B depict, respectively, the detection of the cMCR-1 and cMCR-2 in PBS within the range of 0-50 ng/mL using the sandwich ELISA based on the pAb-mAb-MCR-1-7 configuration. For the cMCR-1 ELISA in the range of 0.01-4 ng/mL, the linear regression had a coefficient of determination $R^2=0.98$ (FIG. 5A inset). For the cMCR-2 ELISA, the linear regression had a $R^2=0.99$ (FIG. 5B inset) in the range of 0.1-6 ng/mL. The average background signal was 563 counts per second (cps) with a standard deviation (SD) of 86.2 for the cMCR-1 ELISA and 833 cps, SD 51.32 for the cMCR-2 ELISA. The limit of detection (LOD) for the cMCR-1 was 0.01 ng/mL and 0.1 ng/mL for the cMCR-2. The ELISA LOD for the cMCR-1 was 10-fold lower than that for the cMCR-2, but the signal to noise ratio for the cMCR-1 was significantly higher than that for the cMCR-2 at all concentrations tested, indicating that this ELISA is more sensitive for detecting the cMCR-1 than the cMCR-2. To evaluate the precision of the sandwich ELISA, the repeatability (intra-day) and reproducibility (inter-day) of the assay for cMCR-1 and cMCR-2 were evaluated. The intra-assay precision expressed as percent coefficient of variation (CV) was less than 5% and the inter-assay precision (% CV) was less than 15% at concentrations within the linear ranges. FDA Center for Biologics Evaluation and Research (CBER) recommends the intra-assay precision determined at each concentration level should not exceed 10% of the CV and the inter-assay precision should not exceed 15% of the CV (FDA. Guidance for industry: Bioanalytical Method Validation; www.fda-.gov/downloads/Drugs/GuidanceCompliance RegulatoryInformation/Guidances/ucm070107pdf. (2001)). The data obtained in this study indicate that the MCR-ELISA is a reliable assay to detect MCR proteins using the novel mAbs of the present invention.

Figure 6:
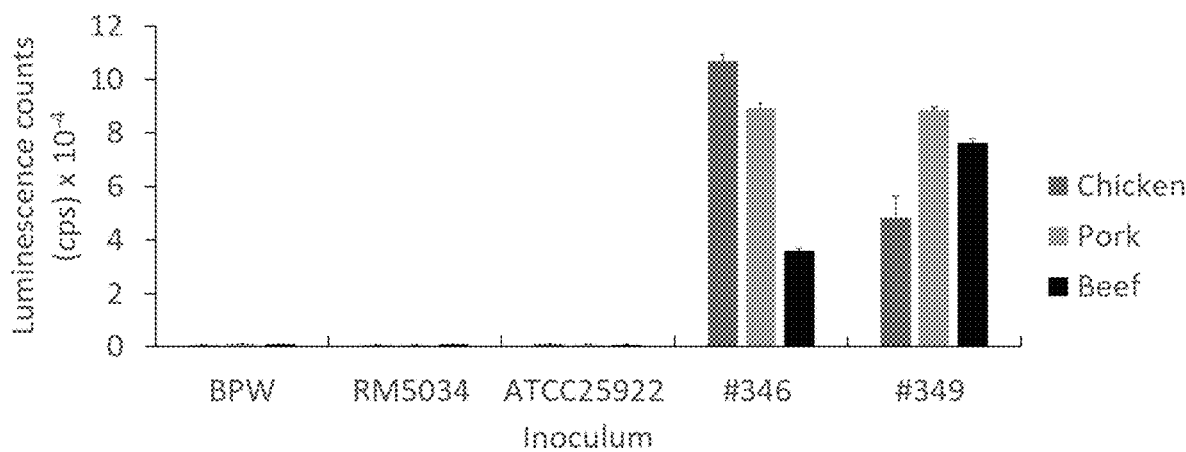
FIG. 6 demonstrates data for the detection of MCR-1 proteins in ground beef, chicken, and pork samples inoculated with bacteria.

Detection of mcr-1 Positive Bacteria in Ground Meats. Plasmid-mediated colistin resistance originated in bacteria associated with food animals (see e.g., Liu, Y. Y. et al., *Lancet Infect Dis* 16, 161-168, doi:10.1016/S1473-3099(15)00424-7 (2016)) and has been found in bacteria isolated from various types of meat worldwide (see e.g., Skov, R. L. & Monnet, D. L. (2016). Euro Surveill 21, 30155, doi: 10.2807/1560-7917.ES.2016.21.9.30155), threatening human health and safety. FIG. 6 demonstrates data for the detection of MCR-1 proteins in ground beef, chicken, and pork samples spiked with bacteria. Negative control (BPW) and bacterial strains were inoculated to meat samples (~10 cfu/25 g), and incubated overnight at 37° C. in Stomacher bags containing 75 mL of TSB with 2 µg/mL colistin. The estimated sensitivity of the ELISA for detection of MCR-1 protein produced by mcr-1 gene carrying bacteria using bacterial culture was demonstrated. The data in Table 2 shows that the ELISA results were positive (above LOD: 227+23×3=296) when cell density was $\geq 0.4 \times 10^6$ for the AR-Bank#346 strain, and $\geq 4 \times 10^6$ cfu/mL for the AR-Bank#349 strain. ELISA results for the mcr-1 gene negative strain, ATCC25922, were negative (below the LOD), at all cell densities tested, even at $8 \times 10^8$ cfu/mL, suggesting this ELISA is specific, and does not cross-react with anything in mcr-1 gene negative bacteria. To validate the ELISA developed in this study for detection of food contamination with the plasmid-borne colistin-resistant bacteria based on the presence of MCR-1 protein in bacterial cells, food samples including ground chicken, pork, and beef were spiked with mcr-1 gene positive and negative strains (10 cfu/25 g). The average luminescence counts (cps) obtained from the negative control, Bacterial Protein Extraction Reagent (B-PER), was 667±80 (n=9). The average counts from the positive control (50 ng/mL cMCR-1 in B-PER) was 751117±15494 (n=9). As shown in FIG. 6, the ELISA counts for chicken, pork and beef samples inoculated with Bacto Peptone Water (BPW, Becton Dickinson Company, Sparks, Md.), ATCC25922, and ATCC29425 were all below the LOD (907 cps). However, significant amounts of MCR-1 protein were detected in samples inoculated with the mcr-1 gene positive strains. The luminescence counts measured from the chicken were 106983±2403 and 48447±7981 for strains AR-Bank #346 and AR-Bank #349, respectively; 89230±1784 and 88727±1036 from the pork; 35940±897 and 76263±1628 from the beef. Compared with ELISA signals obtained for water samples inoculated with AR-Bank #346 (805543±6315) and AR-Bank #349 (679970±6163), the signals obtained from the meat samples were relatively low (7.12 to 13.28% of the signals from the water samples), suggesting there were matrix effects associated with these samples. Nevertheless, this ELISA was sufficiently sensitive to identify colistin-resistant bacteria inoculated in these complex meat samples.

TABLE 2

| Bacterial strain | mcr-1 gene | cfu/mL | Average counts | SD |
|---|---|---|---|---|
| AR-Bank #0346 | + | $4 \times 10^5$ | 407 | 64 |
|  | + | $4 \times 10^6$ | 887 | 107 |
|  | + | $4 \times 10^7$ | 10980 | 1164 |
|  | + | $4 \times 10^8$ | 107503 | 3039 |
|  | + | $8 \times 10^8$ | 555867 | 4447 |
| AR-Bank #0349 | + | $4 \times 10^5$ | 283 | 121 |
|  | + | $4 \times 10^6$ | 490 | 51 |
|  | + | $4 \times 10^7$ | 6693 | 387 |
|  | + | $4 \times 10^8$ | 71373 | 679 |
|  | + | $8 \times 10^8$ | 457703 | 23821 |
| ATCC25922 | − | $4 \times 10^5$ | 170 | 17 |
|  | − | $4 \times 10^6$ | 247 | 23 |
|  | − | $4 \times 10^7$ | 183 | 40 |
|  | − | $4 \times 10^8$ | 263 | 6 |
|  | − | $8 \times 10^8$ | 267 | 55 |
| (−) control (LB:B-PER 1:1) | − | 0 | 227 | 23 |

The recent emergence of mobile colistin-resistance in bacteria and the lack of immunoassays for detection of colistin-resistant gene products (e.g., MCR proteins and variants including MCR-1 protein and MCR-2 protein), provided the impetus for the ongoing commercial need for improved detection. In the present invention, novel polyclonal and monoclonal antibodies with high affinity for MCR-1 and MCR-2 proteins were developed for the first time. A sandwich ELISA established using selected antibodies was shown to offer a unique combination of sensitivity and specificity that allowed detection of as low as about 0.01 ng/mL of MCR protein and identification of MCR protein-producing bacteria using less than $10^6$ cfu/mL of cell culture. The assay was also capable of identifying MCR protein in artificially inoculated ground beef, chicken, and pork with as low as about 10 cfu of colistin-resistant bacteria in 25 g of sample. It is feasible to use this ELISA for detection of MCR proteins in meat samples, as an indicator of the presence of mcr-1 gene-positive bacteria in food animals. This ELISA could be used as a screening method for prospective epidemiological surveys to evaluate the extent and impact of colistin-resistance in food animal borne bacteria.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety, including any materials cited within such referenced materials. Furthermore, the invention encompasses any possible combination of some or all of the various embodiments and characteristics described herein and/or incorporated herein. In addition, the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims. Although any methods and materials similar or equivalent to those described herein can be used in the practice or testing of the present invention, the preferred methods and materials are herein described. Those skilled in the art may recognize other equivalents to the specific embodiments described herein which equivalents are intended to be encompassed by the claims attached hereto.

The claimed invention is:

1. A monoclonal antibody that reacts specifically with at least one mobilized colistin resistance (MCR) protein, wherein the monoclonal antibody is produced by a hybridoma cell line having ATCC Patent Deposit Designation No. PTA-125013; or PTA-125014.

2. The monoclonal antibody or fragment thereof of claim 1 that is isolated and purified.

3. The monoclonal antibody or fragment thereof of claim 1 that is chimeric.

4. The monoclonal antibody or fragment thereof of claim 1, further comprising a label selected from the group consisting of: enzyme labels, radioisotopic labels, non-radioactive isotopic labels, chromogenic labels, fluorescent labels, chemiluminescent labels, and combinations thereof.

5. A hybridoma cell line which produces the monoclonal antibody or fragment thereof of claim 1.

6. The hybridoma cell line of claim 5, wherein the hybridoma cell line is that is selected from the group consisting of: a hybridoma cell line having ATCC Patent Deposit Designation No. PTA-125013; a hybridoma cell line having ATCC Patent Deposit Designation No. PTA-125014.

7. A composition comprising the monoclonal antibody of claim 1.

* * * * *